(12) United States Patent
Rudolph et al.

(10) Patent No.: US 12,305,152 B2
(45) Date of Patent: May 20, 2025

(54) DISPOSABLE CONTAINERS AND REACTION SYSTEMS

(71) Applicant: ABEC, INC., Bethlehem, PA (US)

(72) Inventors: Eric Rudolph, Ambler, PA (US); Peter Silverberg, Southbridge, MA (US)

( * ) Notice: Subject to any disclaimer, the term of this patent is extended or adjusted under 35 U.S.C. 154(b) by 908 days.

(21) Appl. No.: 17/262,997

(22) PCT Filed: Jul. 26, 2019

(86) PCT No.: PCT/US2019/043591
§ 371 (c)(1),
(2) Date: Jan. 25, 2021

(87) PCT Pub. No.: WO2020/023834
PCT Pub. Date: Jan. 30, 2020

(65) Prior Publication Data
US 2021/0324314 A1    Oct. 21, 2021

Related U.S. Application Data

(60) Provisional application No. 62/749,809, filed on Oct. 24, 2018, provisional application No. 62/722,626, filed on Aug. 24, 2018, provisional application No. 62/711,264, filed on Jul. 27, 2018.

(51) Int. Cl.
*C12M 1/00* (2006.01)
*C12M 1/34* (2006.01)
*C12M 3/00* (2006.01)

(52) U.S. Cl.
CPC ............ *C12M 23/14* (2013.01); *C12M 23/28* (2013.01); *C12M 23/48* (2013.01); *C12M 23/50* (2013.01); *C12M 41/40* (2013.01)

(58) Field of Classification Search
CPC ...... C12M 23/14; C12M 23/28; C12M 23/48; C12M 23/50; C12M 41/40
See application file for complete search history.

(56) References Cited

U.S. PATENT DOCUMENTS

| 5,638,989 A | * | 6/1997 | Ophardt | A47K 5/1214 222/105 |
|---|---|---|---|---|
| 7,740,212 B2 | | 6/2010 | Austin et al. | |
| 2009/0188211 A1 | | 7/2009 | Galliher et al. | |

(Continued)

FOREIGN PATENT DOCUMENTS

| JP | H0830367 A | 2/1996 |
|---|---|---|
| WO | 2011071897 A2 | 6/2011 |

OTHER PUBLICATIONS

International Application No. PCT/US2019/043591, International Search Report and Written Opinion mailed Nov. 15, 2019, 11 pages.

*Primary Examiner* — Liban M Hassan
(74) *Attorney, Agent, or Firm* — Patrick J. Halloran

(57) ABSTRACT

This disclosure relates to equipment utilized to manufacture chemical agents, particularly biopharmaceuticals, using Disposable Containers (DCs), and particular those used for storing and/or supplying buffers and other solutions in systems for carrying out reactions in reaction vessels. In some embodiments, the DC comprises a first and second end, one or more attachment connectors at the first end, and one or more conveyance connectors at the second end. Systems comprising and methods for using and/or testing the same are also disclosed.

4 Claims, 7 Drawing Sheets

(56) References Cited

U.S. PATENT DOCUMENTS

| | | |
|---|---|---|
| 2009/0290962 A1 | 11/2009 | Fisher et al. |
| 2010/0062522 A1 | 3/2010 | Fanning et al. |
| 2010/0149908 A1 | 6/2010 | Singh et al. |
| 2015/0135643 A1 | 5/2015 | Cox et al. |
| 2016/0272931 A1 | 9/2016 | Rudolph et al. |

* cited by examiner

Prior art (US 2016/0272931)

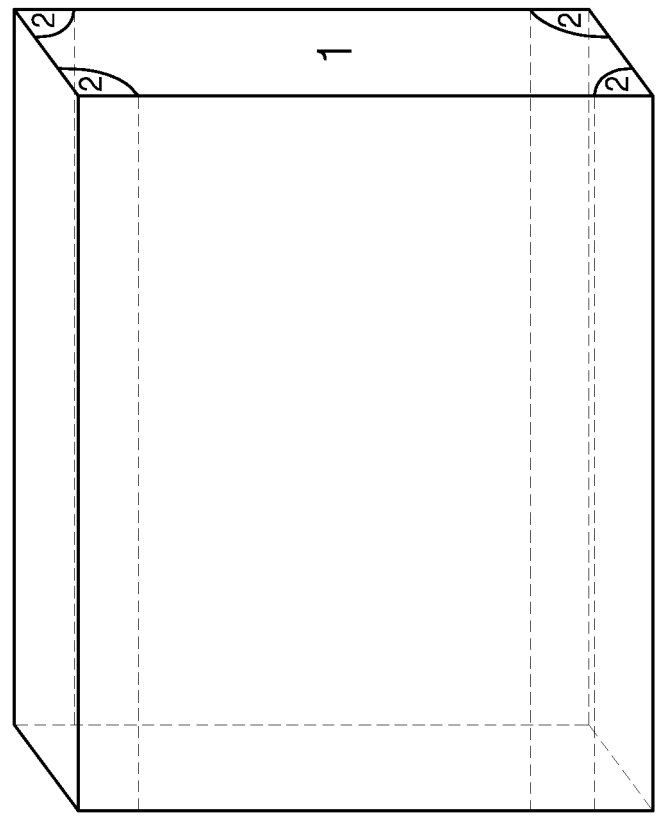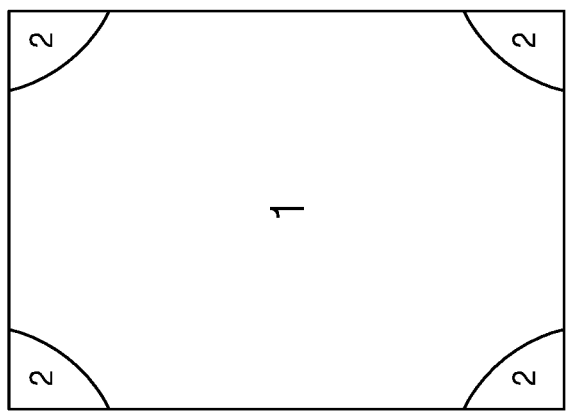
FIG. 4C

DISPOSABLE CONTAINERS AND REACTION SYSTEMS

RELATED APPLICATIONS

This application is the National Stage Application under 35 U.S.C. § 371 of International Application No. PCT/US2019/043591 filed Jul. 26, 2019, which claims priority to U.S. Ser. No. 62/711,264 filed on Jul. 27, 2018; U.S. Ser. No. 62/722,626 filed on Aug. 24, 2018; and, U.S. Ser. No. 62/749,809 filed on Oct. 24, 2018; the entire contents of which are being incorporated herein in their entireties.

FIELD OF THE DISCLOSURE

This disclosure relates to equipment utilized to manufacture chemical agents, particularly biopharmaceuticals, using Disposable Containers (DCs), and particular those used for storing and/or supplying buffers and other solutions in systems for carrying out reactions in reaction vessels.

BACKGROUND OF THE DISCLOSURE

This disclosure relates to devices and methods for the manufacture of chemical and/or biological products Such as biopharmaceuticals using Disposable Containers (DCs). For instance, fermentors or bioreactors commonly provide a reaction vessel for cultivation of microbial organisms or mammalian, insect, or plant cells to produce such products. This disclosure provides improved systems and parts for use in such systems (or other systems).

BRIEF DESCRIPTION OF THE DRAWINGS

FIG. 4. Illustrative embodiments of disposable container in the deployed configuration, the disposable container comprising at least one first chamber and at least one second chamber separated from one another by a partition, the first chamber being configured to hold a greater volume of fluid than the second, the second chamber being connected to an air source, the disposable container being deployed (e.g., unrolled) from the undeployed (e.g., rolled) configuration by the injection of air into at least one second chamber.
FIG. 4C. Exemplary DC with exemplary second channel/chamber arrangements.

SUMMARY OF THE DISCLOSURE

Figure 1:
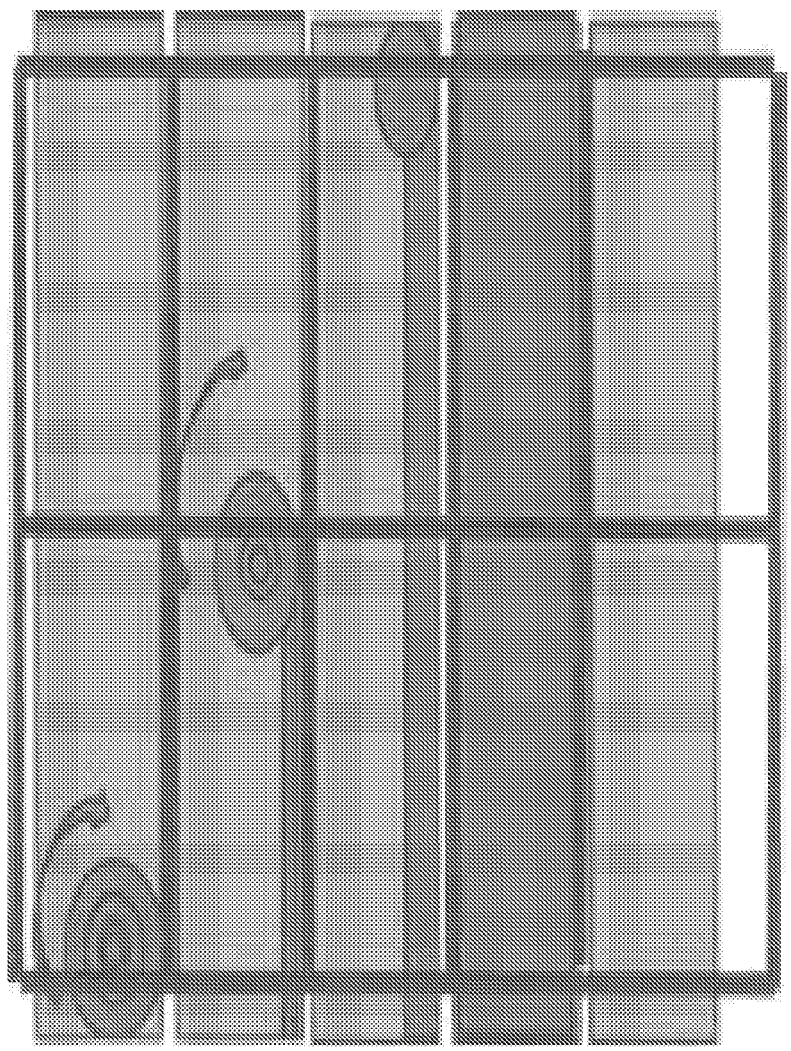
FIG. 1. Horizontal deployment of disposable container within a holder.

This disclosure relates to equipment utilized to manufacture chemical agents, particularly biopharmaceuticals, using Disposable Containers (DCs), and particular those used for storing and/or supplying buffers and other solutions in systems for carrying out reactions in reaction vessels.

DETAILED DESCRIPTION OF THE INVENTION

This disclosure relates to equipment utilized to manufacture chemical agents, particularly biopharmaceuticals, using Disposable Containers (DCs), and particular those used for storing and/or supplying buffers and other solutions in systems for carrying out reactions in reaction vessels. In some embodiments, the DCs described herein may be incorporated into systems using, for instance, reaction vessels and components described in, for example, U.S. Pat. No. 9,228,165 B2 (ABEC, Inc.), U.S. Pat. No. 8,658,419 B2 (ABEC, Inc.), U.S. Pat. Pub. US 2016/0272931 A1, and/or U.S. Ser. No. 62/690,281 (ABEC, Inc.) within reaction vessels that comprise DCs in which reactions are carried out (disposable reaction container, or "DRC"). In some embodiments, the DCs described herein may supply fluids (e.g., one or more buffers) to such a reactor system. An exemplary reactor system may comprise a mobile carriage assembly comprising: an implement (e.g., at least one wheel or track) for fixably attaching the mobile carriage assembly to a holder, the holder comprising a receiving implement (e.g., one or more sliding surfaces (e.g., as may be found in a drawer), and/or at least one or more wheels and/or tracks) for receiving the mobile carriage assembly, an interior, and a door; wherein: the interior of the holder maintains the desire geometry of the disposable reaction container; and, the door of the holder contains the disposable reaction container in the interior of the holder. In some embodiments, the DCs described herein may supply fluids (e.g., one or more buffers) to a reactor system comprising: a) a mobile carriage assembly holder into which a mobile carriage assembly may be removably inserted, the holder comprising a receiving implement; b) a mobile carriage assembly comprising: i) at least one primary mobility implement in contact with the ground, and providing mobility to the mobile carriage assembly, prior to insertion of the mobile carriage assembly into the holder; ii) secondary mobility implements, wherein: 1) the secondary mobility implements are not in contact with the ground prior to or following insertion of the mobile carriage assembly into the holder; 2) at least one secondary mobility implement is proximal to the receiving implement and at least one secondary mobility implement is distal from the receiving implement prior to insertion of the mobile carriage assembly into the holder; 3) the secondary mobility implements provide for insertion of the mobile carriage assembly into, and removal of the mobile carriage assembly from, the holder using the receiving implement; and, iii) a shaft and impellar assembly; and, c) a disposable reaction container (DRC) enclosing the shaft/impellar assembly; wherein the holder: comprises a heat transfer jacket; provides for heating and/or cooling of the reaction components within the DRC; comprises a door for maintaining the DRC separated from the exterior of the holder; and, comprises one or more anti-swirl and/or heat exchange baffles. In some embodiments, the reaction vessels may comprise a coalescer that may also comprise, or be connected and/or attached to a device comprising mesh and/or packed solids (e.g., an "anti-foaming device", as described in US Pat. Pub. No. 2016-0272931 A1 (Rudolph, et al.)) Such a device may be positioned, e.g., between the DRC and the one or more coalscer(s) such that humidified gas passes through the anti-foaming device before entering the one or more coalescers, between coalescers, within a coalescer, or between a coalesce and any other part of the systems described herein (e.g., a filter). In some embodiments, and as described in US Pat. Pub. No. 2016-0272931 A1, the anti-foaming device may comprising a container, the interior volume of which may include static mixer and/or granules (e.g., tortuous path) that collapse the foam (e.g., in the form of bubbles) that enters the anti-foaming device. The anti-foaming device typically includes an inlet receiving surface and a venting surface positioned opposite one another on either side of the chamber. The tortuous pathway is found within the chamber between the inlet surface and the venting surface of the anti-foaming device. The chamber may be in the form of tubing (e.g., plastic tubing), for example. Each of the gas inlet surface and the venting surface may be comprised of a material (e.g., a porous and/or mesh material) which serves to retain the granules. The material comprising the surfaces of the same may thus serve to compartmentalize the granules, thereby forming a container. In some embodiments, the anti-foaming device may be contained within a portion of tubing connected to the RDC between the exhaust port at the top of the RDC and before the exhaust. In such embodiments, the anti-foaming device does not necessarily need to form a completely separate piece of equipment but may instead exist within a piece of tubing through which the humid gas and/or fluid migrates out of the second zone (HS). In such embodiments, the anti-foaming device may be formed by positioning the material at either ends of a section of tubing that contains a tortuous fluidic pathway. One piece of said material may be positioned within the tubing to be proximal to the RDC and distal to the vent, and function as a gas stream receiving surface. Another piece of material may be positioned within the tubing to be proximal to the vent and distal to the RDC, and function as a venting surface. The tortuous fluidic pathway is thereby positioned between the gas stream receiving surface and the venting surface. In some embodiments, the tortuous fluidic pathway, the tubing, the material, and/or the DC are composed of substantially the same material. Alternatively, the anti-foaming device may be manufactured and then inserted into the tubing, for instance. In some such embodiments, humid gas migrating from the second zone (HS) encounters the anti-foaming device before entering the coalescer (e.g., the anti-foaming device is positioned between the second zone (HS) and the coalescer, and provides a gas outlet). A system may comprise one or more than one of such devices, e.g., a single device attached to the single coalescer of the system, multiple devices attached to the one or each one of the coalescer(s) of the system, and/or single individual devices being attached to multiple and/or each of multiple coalescers of the system. In some embodiments, then, the system may comprise a RDC comprising a second zone (HS) from which the humid gas migrates through this device and into the coalescer. Other embodiments may also be suitable, as would be understood by those of ordinary skill in the art.

The reactors to which the DCs described herein can supply buffers and/or other materials (e.g., solutions) are typically, but not necessarily, constructed of metal and usually, but not necessarily, from a corrosion-resistant alloy. For instance, suitable materials may include, without limitation, sheet/plate stock (and/or dimple-jacket material for, e.g., heat transfer systems). Suitable exemplary materials include, for example, carbon steel, stainless steel (e.g., 304, 304L, 316, 316L, 317, 317L, AL6XN), aluminum, Inconel® (e.g., Inconel 625, Chronin 625, Altemp 625, Haynes 625, Nickelvac 625 and Nicrofer 6020), Incoloy®, Hastelloy (e.g., A, B, B2, B3, B142T, Hybrid-BC1, C, C4, C22, C22HS, C2000, C263, C276, D, G, G2, G3, G30, G50, H9M, N, R235, S, W, X), and Monel®, titanium, Carpenter 20®, among others. It is understood, however, that other materials besides or in addition to a corrosion-resistant alloy such as, but without limitation, plastic, rubber, and mixtures of such materials may also be suitable. A "mixture" of materials may refer to either an actual mixture per se to form a combined material or the use of various materials within the system (e.g., an alloy reactor shell and rubber baffle components). Other systems, reaction vessels, components, and the like may also be suitable as may be determined by those of ordinary skill in the art.

The parts of the systems described herein may be connected to one another by welding or other similar processes, using a flexible material such as tubing (e.g., of a type standard in the industry), and/or using the connectors and other arrangements described herein. Those of ordinary skill in the art would understand such connection techniques.

The DCs described herein are typically comprised of a flexible material that is rigid and water impermeable such that a reaction may be carried out within an internal reaction chamber (or internal volume) that is surrounded by the flexible material, and that maintains (e.g., does not lose) its integrity during such reaction, that can be and is typically disposed of (e.g., removed from the reaction vessel) after use. The DC is physically supported by the reaction vessel (e.g., which may also be referred in some embodiments as a DC "holder" or "housing") and/or associated components, and typically includes and/or is attached to components allowing for attachment of it to the reaction vessel. The DC is also sealable so that sterile processes may be carried out within the same such that, e.g., failure is not caused by hydraulic forces applied thereto when it is filled with fluid. In some embodiments, the DC may be comprised of a flexible, water impermeable material such as a low-density polyethylene having a thickness in a range between about 0.1 mm to about 5 mm, or other appropriate thickness. The material may be arranged as a single or in multiple layers (e.g., single- or dual-ply). Where a DC comprises multiple layers, it may be comprised of two or more separate layers secured together by, e.g., an adhesive. Exemplary materials and arrangements that may be used include but are not limited to polyethylene, polypropylene, PVC, ABE, and/or any described in, for instance, U.S. Pat. Nos. 4,254,169; 4,284,674; 4,397,916; 4,647,483; 4,917,925; 5,004,647; and/or 6,083,587; and/or U.S. Pat. Pub. No. US 2002-0131654 A1. The DC may be manufactured to have any desired size (e.g., 10 liters, 30 liters, 100 liters, 250 liters, 500 liters, 750 liters, 1,000 liters, 1,500 liters, 3,000 liters, 5,000 liters, 10,000 liters or other desired volumes).

DCs are manufactured using film supplied at limited widths, typically requiring the welding panels of film together to produce a DC of sufficient size. Typically, such panels are welded to one another such that the weld or resulting seam is along the central axis of the DC. In some embodiments, a DC as described herein may be constructed from two or more pieces of material (e.g., DC sections) to provide an asymmetrically-positioned implement port (or fixture access point). In certain embodiments, one or more of the DC wall sections are constructed as a single piece of material (e.g., flexible material). Two or more such DC wall section(s) may then be adjoined to one another to form the walls of the DC. For instance, two wall sections may be adjoined to one another along a central axis at which a seam is formed between the sections to form the DC. Where three, four or more wall sections are provided, each of the sections may be adjoined to at least one or two other sections along at least two different axes (e.g., seams) such that the sections collectively form the DC. The implement port may be positioned proximal to an end of one of the sections but distal from the central axis (and/or any other axis comprising a seam) at which the DC wall sections are adjoined to one another (e.g., the seam(s)). Thus, this asymmetrically-positioned implement port is typically found within one of the wall sections (e.g., a wall subsection) but off of, or away from, a seam at which any two DC wall sections are adjoined to each other. The orifice comprises an interior surface and an exterior surface. The interior surface of the orifice is found within the interior chamber of the DC once the DC wall sections are adjoined to one another. The exterior surface of the orifice is found on the exterior of the DC once the DC wall sections are adjoined to one another. In some embodiments, one or more of the DC wall sections may comprise a lifting tab that may be used during the adjoining process to lift each section into position such that one section may be adjoined to another section or for another use. One or more of the DC wall sections may comprise one or more ports through which additional implements may be attached to and/or introduced into the DC.

In some embodiments, this disclosure relates to horizontal deployment system for use with disposable containers (DCs). DCs are typically positioned vertically within a container are typically filled from the bottom to the top using a hoisting mechanism that serves to raise the DC as it is being filled. However, a DC may also be filled such that it expands into a container/holder horizontally (see FIG. 1 and, e.g., US 2016/0272931 A1). This may be accomplished by, for instance, positioning the DC at one end of a horizontal container and filling the DC such that it expands horizontally across the container. The DC may be in any configuration prior to filling but one particularly useful configuration may be as a roll. If filled from the rolled configuration, the DC may conveniently unroll horizontally across the horizontal container. In some embodiments, the horizontal container may be a horizontal holding tank comprising a housing comprising an at least partially open panel and a closed panel; a rolled sterile DC positioned adjacent to the at least partially open panel of housing; and, inlet and outlet tubing protruding through the at least partially open end of the housing. Typically, the inlet tubing comprises a sterile filter such that any fluid entering the DC would be (e.g., or become) sterile. This device may therefore be used to position a rolled sterile single use container proximal to the partially open panel and distal from the closed panel. The DC is then filled with a sterile fluid (e.g., either already sterile or sterilized as it passes through the sterile filter) through the inlet tubing such that it unrolls horizontally from the partially open panel toward the closed panel of the housing as it is filled.

In some embodiments, this disclosure provides a system comprising: a disposable container comprising a first and second end, one or more attachment connectors at the first end, and one or more conveyance connectors at the second end; a holder for containing the disposable reaction container, the holder comprising: upper and lower surfaces, and optionally side surfaces, each comprising an interior surface and an exterior surface; a front section and a rear section, each section comprising about one-half the length of the holder; one or more receiving connectors positioned near the front section for receiving the one or more attachment connectors of the disposable container; at least one means for conveying (i.e., a means of conveyance such as a mechanism or device, such as one or more cables, lines, strings, ropes, chains, treads (e.g., an adhesive tread), and/or the like) the disposable container from the undeployed to the deployed configuration, optionally wherein the at least one mechanism is positioned closer to the rear section than the front section; and, at least one means of conveyance connected to the disposable container by the one or more conveyance connectors; wherein: the disposable container is positioned upon the inner surface of the holder; when the disposable container is in the undeployed configuration, engagement of the means of conveyance changes the configuration of the disposable container from the undeployed position (e.g., rolled or unrolled) to the deployed position (e.g., unrolled or unfolded), wherein the disposable container is extended along at least part of the length of an inner surface of the holder; and, optionally, the means of conveyance is attached to the disposable container by the one or more conveyance connectors.

Figure 2:
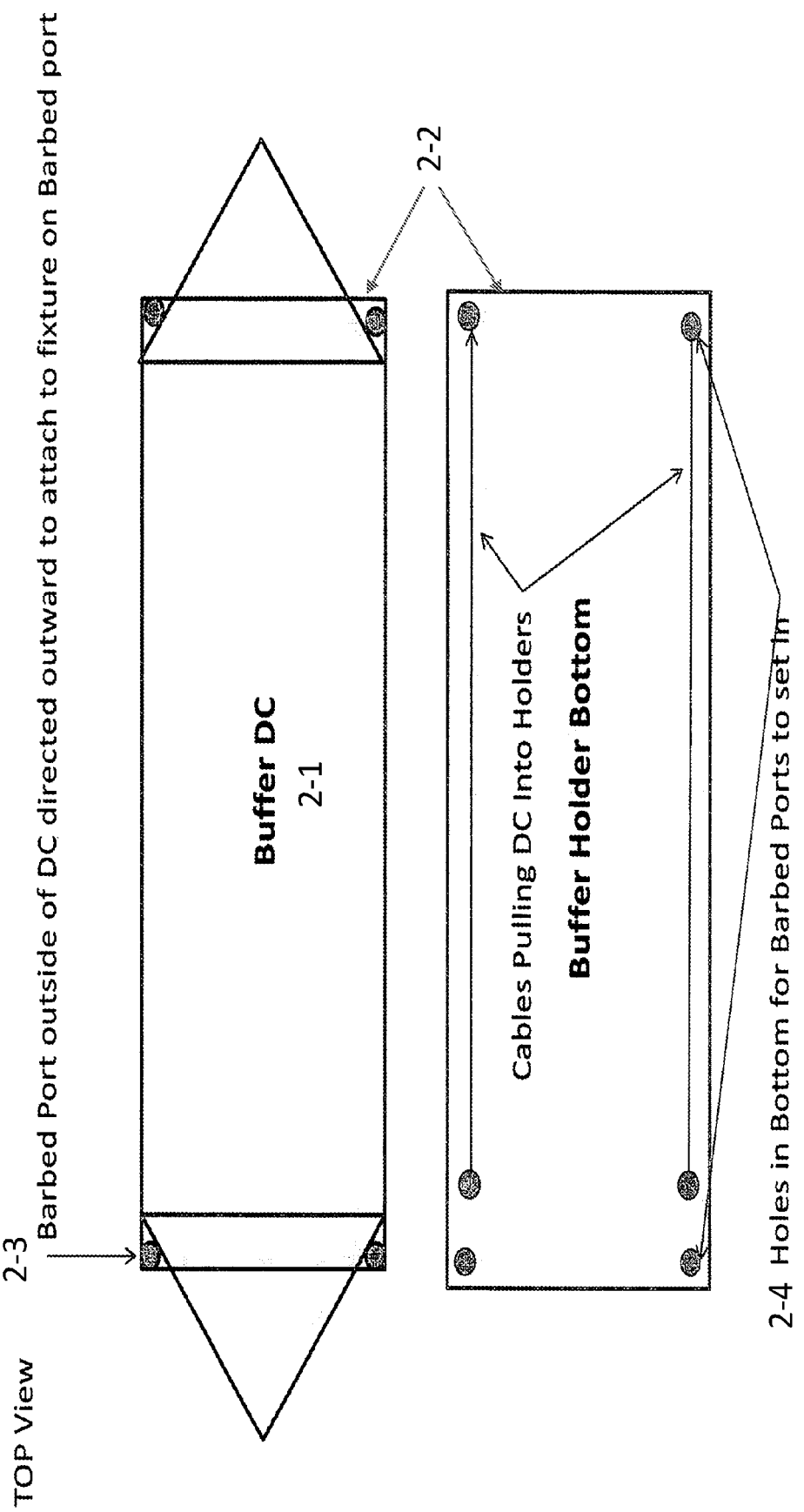
FIG. 2. Top views of illustrative embodiment.

In some embodiments, this disclosure provides a system such as a reaction or container system comprising and DC and a DC holder for "holding" and/or containing the DC (which may be referred to herein simply as the "holder"; e.g., a container such as a reusable container, preferably constructed of an essentially inflexible or at least less flexible material as compared to the DC), the system comprising:

a) at least one DC comprising an internal volume surrounded by DC material (e.g., in which a reaction is to be carried out), a first and second opposite ends, upper and lower surfaces of DC material (between which the reaction chamber or internal volume is formed), preferably each being separated from the internal volume of the DC (e.g., each being present within a sealed edge of the DC), one or more DC attachment connectors positioned at the first end, and one or more DC conveyance connectors positioned at the second end;

b) a DC holder comprising: 1. a holder floor (e.g., upon which the DC can be supported and/or rests); 2. an interior surface and an exterior surface (e.g., of the holder floor); 3. a holder front section and a holder rear section; 4. optionally one or more holder side surfaces; 5. one or more holder receiving connectors positioned near the holder front section for receiving the one or more DC attachment connectors, preferably positioned upon the holder inner lower surface (e.g., floor) or holder sidewalls; and, 6. at least one orifice in the holder being positioned near the rear section and connecting and/or traversing the holder inner surface, preferably the floor, and the outer surface of the holder; where b1-b4 above together form (e.g., surround) a holder inner chamber (e.g., into which the DC is deployed in use); and, d) at least one means of conveyance, mechanism, and/or device traversing the orifice and being attached to the DC using the one or more DC conveyance connectors (e.g., a cable as illustrated in FIG. 2 ("Cables Pulling DC Into Holder")), and being for conveying, deploying and/or moving (which may be used in the alternative) the DC horizontally into or through the holder inner chamber.

In some embodiments, the DC can be positioned upon the inner surface (e.g., inner bottom surface or floor) of the holder, in the undeployed and/or deployed position (preferably when in either position), and attached thereto by one or more DC attachment connectors. Preferably the one or more DC attachment connectors are positioned on the lower surface of the DC and the one or more holder receiving connectors are positioned on the holder floor such that the DC is attached to the holder floor by a connection between one or more of the DC attachment connectors and the one or more holder receiving connectors. Preferably, the DC attachment connectors and DC conveyance connectors are positioned upon or connected to the DC outside of the material forming the DC reaction chamber or DC internal volume so as not to jeopardize the integrity thereof (e.g., on a DC edge, such as a sealed edge). The DC can be positioned in the holder in the undeployed configuration in the front section of the container, and the DC can be conveyed, deployed and/or moved (e.g., horizontally) into or through the DC holder using one or more means of conveyance (e.g., one or more cable(s), line(s), string(s), rope(s), chain(s), tread(s) (e.g., an adhesive tread), telescoping rods, screws, pulleys, and/or the like, optionally including a manual or automatic cable roller) extending from the holder back section to the holder front section (e.g., traversing or extending through the orifice in the holder floor, the cables and the like extending toward the user along the exterior of the holder floor) connected to one or more of the DC conveyance connectors. In the undeployed configuration, the one or more DC conveyance connectors can be connectors (e.g., cable connectors) positioned near the front section of the holder (as the DC is not yet deployed, typically in a rolled or folded configuration). Where a cable or the like is used, for instance, it can extend through the orifice and along the inner surface of the holder to the front section thereof and can be attached to the DC by the one or more DC conveyance connectors (e.g., cable connectors), and can be grasped by a user and/or connected to a device (e.g., an automated device) typically positioned nearer to the front section of the holder than to the back section thereof. The application of a pulling force upon the DC conveyance connectors and/or cable or the like from the rear section, by virtue of the cable or the like extending into the holder interior chamber front section from the back section, moves the DC via the DC conveyance connector(s), thereby extending the DC from the undeployed configuration in the front section of the holder towards the rear section of the holder and into the deployed position (e.g., to position the DC in the deployed position). Thus, in some embodiments, the DC is positioned upon the inner surface (e.g., floor) of the holder, and attached to the holder by the one or more DC attachment connectors and holder receiving connectors; wherein the application of a pulling force upon the cable or the like from the rear section moves the DC conveyance connector(s) and at least the front end of the DC from the front section of the holder towards the rear section of the holder to position the DC in the deployed position within the holder interior chamber.

In some embodiments, the disposable container and/or the holder of such systems are of an essentially square, rectangular, oval or circular shape. In some embodiments, such as those in which the DC is in the undeployed position, the one or more DC conveyance connectors are positioned closer to the front section of the holder than the back section of the holder, as are the corresponding holder receiving connectors. In some embodiments, the DC is attached to the holder by connection of one or more DC attachment connectors and one or more holder receiving connectors. In some embodiments, the corresponding one or more DC attachment connectors and one or more holder receiving connectors form a matching pair(s) (e.g., system) suitable for reversible connection to one another (e.g., each comprising opposite members of a velcro system or barbed port/connector pair). In some embodiments, the means of conveyance is attached to the DC by the one or more DC conveyance connectors. In some embodiments, the application of a pulling force upon the means of conveyance (e.g., a cable) from the rear section moves the DC conveyance connectors (e.g., cable connector) and DC from the front section of the holder towards the rear section of the holder to position the DC in the deployed position (e.g., from the undeployed position). In some embodiments, such as when the DC is positioned in the container in the undeployed configuration within the front section of the container, the one or more DC conveyance connectors are positioned closer to the front section of the holder than the back section; the means of conveyance comprises one or more cables or the like extending through an orifice positioned in the back section of the holder and along the inner surface thereof, the one or more cables or the like being connected to the disposable container by the one or more conveyance connectors, one or more of the conveyance connectors optionally being a cable connector; and, the application of a pulling force upon the cable from the rear section moves the cable connector and disposable container from the front section of the holder towards the rear section of the holder to position the DC in the deployed position. In some embodiments, one or both of the one or more attachment connectors and/or the DC conveyance connector comprise a barb port. In some embodiments, the means or mechanism for conveying the disposable container is one or more cables, one or more telescoping rods, and/or one or more screws. In some embodiments, the mechanism for conveying the disposable container from the undeployed to the deployed configuration comprises an orifice in the holder and a cable connected to the disposable container and traversing said orifice. In some embodiments, the mechanism for conveying the disposable container further comprises a manual or automatic cable roller. In some embodiments, the cable extends through the orifice and is attached to the DC using the one or more DC conveyance connectors. In some embodiments, the cable and/or the like extends along the inner surface of the holder when the DC is in the undeployed position. In some embodiments, the cable or the like extends through the orifice and along the inner surface of the holder to the front section and is attached to the disposable container by the one or more cable connectors. In some embodiments, the mechanism for conveying the disposable container comprises one or more pulleys.

In some embodiments, the DC is in fluid communication with at least one source of fluid (e.g., comprising a buffer) that is deposited into the DC. In some embodiments, the DC is in fluid communication with at least one reaction vessel. In some embodiments, the DC is in fluid communication with at least one external source of fluid that is deposited into the DC, and is in further fluid communication with at least one reaction vessel. In some embodiments, the DC comprises one or more fluids, optionally a buffer, within an interior chamber of the DC. In some embodiments, the DC comprises at least one port, optionally multiple ports. In some embodiments, the DC comprises multiple ports, at least one of said ports being in fluid communication with at least one source of fluid that is deposited into the DC and at least one of said ports is in fluid communication with at least one reaction vessel. In some embodiments, the one or more ports comprises a barbed port. In some embodiments, multiple units comprising at least one DC and at least one holder, optionally wherein the DC and/or holder of at least one unit is in contact with at least one DC and/or holder of at least one other unit. In some such embodiments, at least one DC is in fluid communication with at least one other DC.

Figure 3:
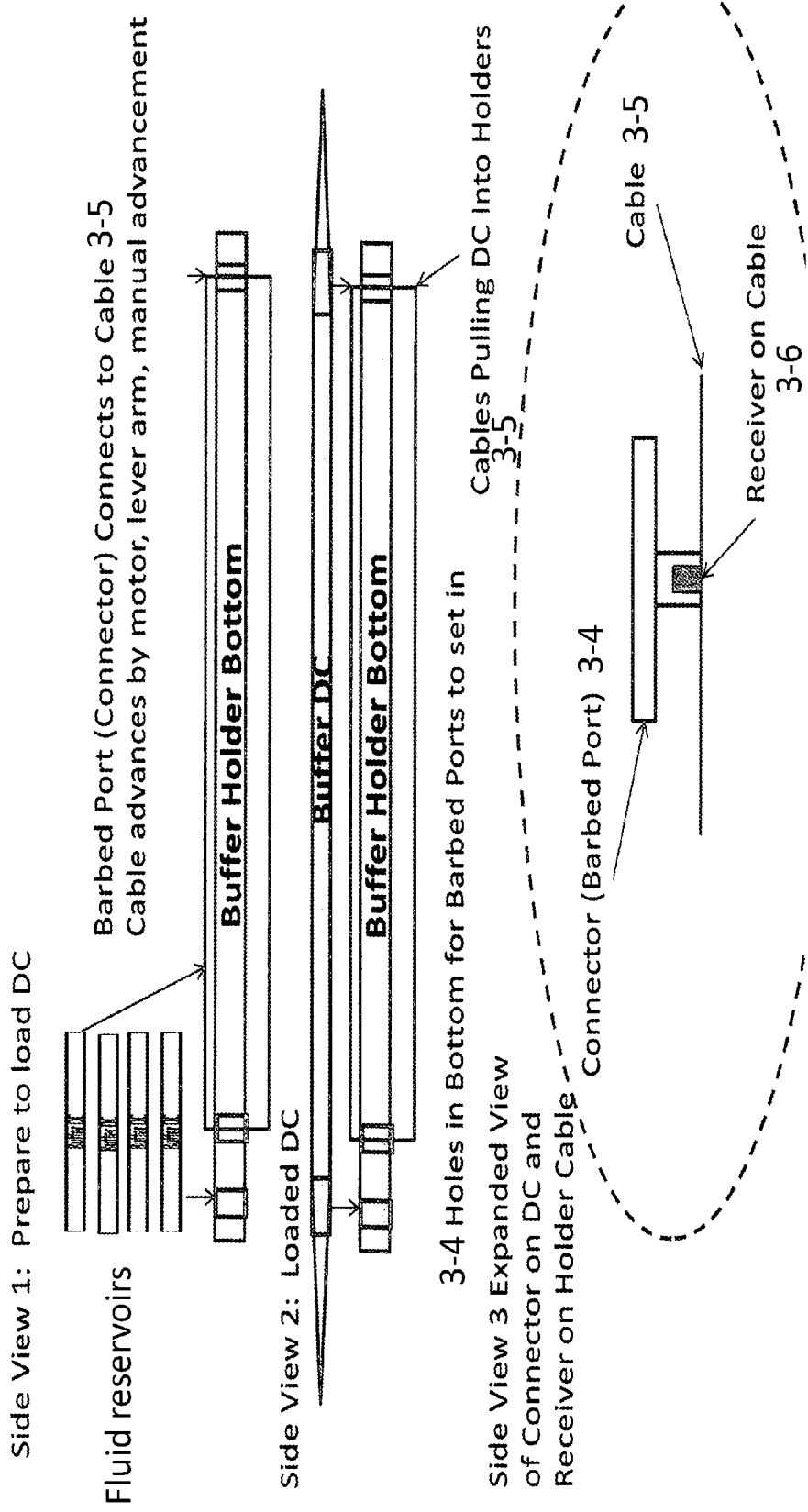
FIG. 3. Side views of illustrative embodiment.

This disclosure also provides DC(s) comprising one or more attachment connectors and one or more DC conveyance connectors. In some embodiments of such DCs, the DC attachment connectors are suitable for attachment to a separate disposable container holder (e.g., via one or more holder receiving connectors). In some embodiments of such DCs, the attachment connectors are suitable for attachment to a mechanism for conveying the DC from an undeployed to a deployed configuration within a DC holder. In some embodiments of such DCs, one or more of the DC attachment connectors comprises a barbed port. In some embodiments of such disposable container(s), the DC attachment connectors are welded to the DC. In some embodiments of such DCs, the DC comprises an interior surface and an exterior surface, the interior surface surrounding (e.g., forming) at least one internal chamber, and said DC attachment connectors are positioned on the exterior surface. In some embodiments of such DCs, the DC is comprised of two or more sheets of material adjoined to one another along at least one edge, and at least one or more of the DC attachment connectors are positioned within at least one of said edges, outside of the areas surrounding the internal chamber. In some embodiments of such DCs, the DC comprises a first end and a second end opposite the first end, the one or more DC attachment connectors are positioned at the first end, and the one or more DC conveyance connectors are positioned at the second end. In some embodiments of such DCs, the DC is attached to a DC holder by a connection between the one or more DC attachment connectors and one or more holder receiving connectors. In some embodiments of such DCs, the DC is attached to a means (e.g., mechanism) for conveying (e.g., moving from an undeployed to a deployed position) the DC by the one using the one or more DC conveyance connectors. In some embodiments of such DCs, the DC is attached to a means (e.g., mechanism for conveying the disposable container that is one or more cables, one or more telescoping rods, and/or one or more screws, and/or the like. In some embodiments of such DCs, the one or more DC attachment connectors and/or the one or more DC conveyance connectors can comprise a barbed port. In some embodiments, such a barbed port can be attached to the holder receiving connector which can, in some embodiments, be an orifice (i.e., hole) in the lower surface of the holder into which the barb can be inserted, affixed, and/or connected. An illustrative embodiment is illustrated in FIG. 2, which shows a DC filled for containing buffer ("Buffer DC" (2-1)) within a holder (2-2) via a DC attachment connector (barbed port (2-3) connected to holes in the holder (2-4)); and exemplary cables connected to DC conveyance connectors for moving the DC from the undeployed to the deployed position. An illustrative embodiment is also illustrated in FIG. 3, which shows an exemplary means of conveyance (cable 3-5) connected to DC attachment connector (barbed port (3-3)), cable (3-5) comprising one or more receivers (3-6) for DC attachment connector (barbed port (3-3)), where the cables extend through holes in the holder bottom surface (3-4). Embodiments that vary from those illustrated in FIGS. 2-3 are also contemplated as would be understood by those of ordinary skill in the art.

In some embodiments of such DCs, the DC has an essentially square, rectangular, oval or circular shape. In some embodiments of such DCs, the DC has a capacity of 10 to 10,000 liters, optionally 10 liters, 30 liters, 100 liters, 250 liters, 500 liters, 750 liters, 1,000 liters, 1,500 liters, 3,000 liters, 5,000 liters, or 10,000 liters. In some embodiments, the DC is in fluid communication with at least one external source of fluid. In some embodiments, the DC is in fluid communication with at least one reaction vessel. In some embodiments, the DC is in fluid communication with at least one external source of fluid and at least one reaction vessel. In some embodiments, the DC further comprises an interior chamber suitable for comprising, or in some embodiments comprising, one or more fluids, optionally a buffer, within the interior chamber. In some embodiments, the DC comprises at least one port, optionally multiple ports. In some embodiments, the DC comprises multiple ports, at least one of said ports being in fluid communication with at least one external source of fluid and at least one of said ports is in fluid communication with at least one reaction vessel. In some embodiments, at least one of said ports is a barbed port. In some embodiments, the DC(s) is/are in fluid communication with at least one other DC and/or at least one reaction vessel.

In any of the systems described herein, a DC in the "undeployed" configuration is one that is essentially unsuitable for filling with a fluid by virtue of it being, for instance, being in the rolled position, or being compressed "accordion-style", or the like such that the interior chamber is not open (e.g., the opposing sides of the DC that together surround the interior chamber are substantially adjacent to one another). Changing the configuration of the DC to the deployed position (i.e., horizontally as described herein) allows for fluid to more easily enter the interior chamber. The DCs described herein typically include one or more ports for filling the interior chamber with fluid from an external source (e.g., a supply tank containing such a fluid (e.g., a buffer)). The one or more ports may be positioned anywhere on the DC and may be positioned to take advantage of gravity in the filling and/or emptying of the DC. In some embodiments, the DC may be filled from the front section such fluid enters and fills the DC from the front section of holder toward the back section of the holder and then up from the top to bottom sections of the holder. Other methods for filling the DCs described herein may also be suitable, as would be understood by those of ordinary skill in the art.

Thus, in some embodiments, this disclosure provides an apparatus comprising a housing comprising an at least partially open panel (preferably at the front section of the holder) and a closed panel (preferably at the back section of the holder); a rolled sterile single use disposable container (i.e., DC): positioned adjacent to the at least partially open panel of housing (i.e., holder); and, comprising inlet and outlet tubing protruding through the open end of the housing, the inlet tubing comprising a sterile filter. Also provided are methods comprising positioning a rolled sterile single use container (i.e., DC) within a housing comprising a partially open panel and a closed panel, the container being arranged such that the container to unrolls horizontally from the partially open panel toward the closed panel, the container comprising inlet and outlet tubing arranged opposite the closed end and protruding through the open end, the inlet tubing comprising a sterile filter; and, filling the DC with a sterile fluid through the inlet tubing and sterile filter such that the container unrolls horizontally from the partially open panel toward the closed panel of the housing as the fluid fills the DC.

Figure 4A:
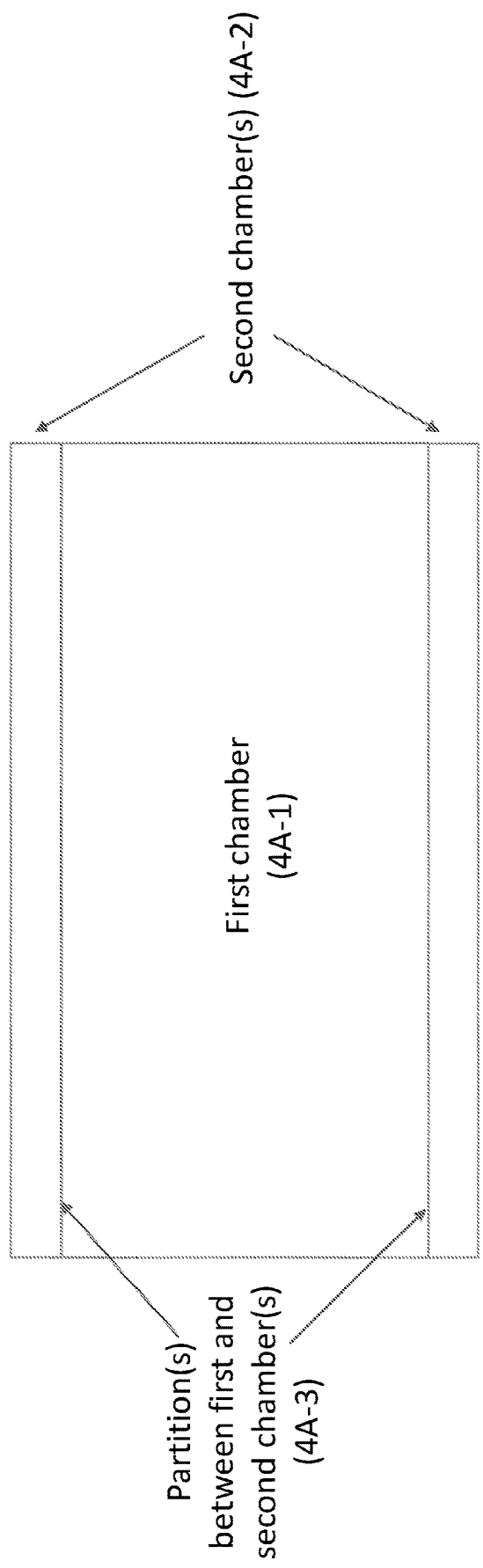
FIG. 4A. Exemplary DC.
Figure 4B:
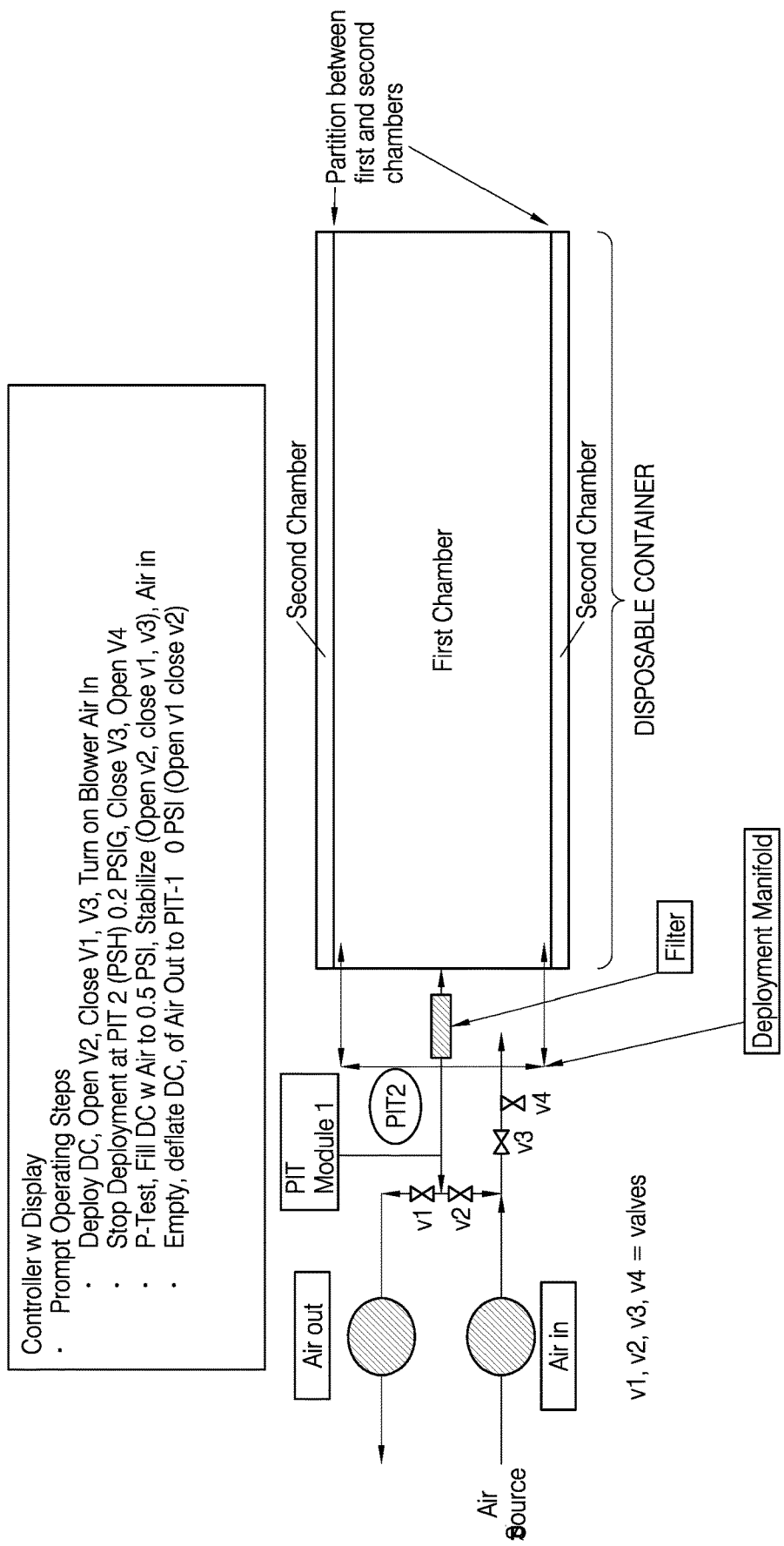
FIG. 4B. Exemplary DC and system.
Figure 5:
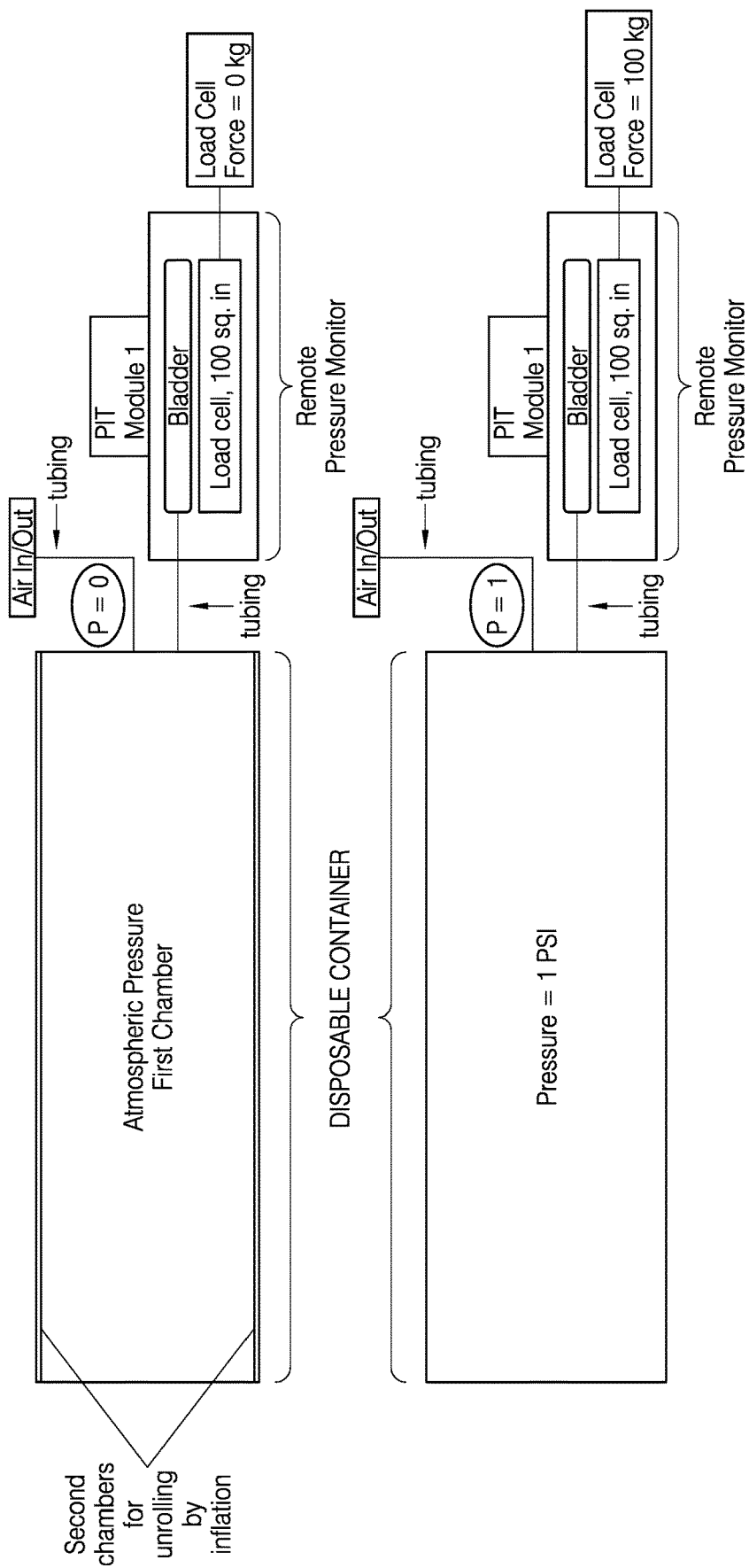
FIG. 5. Illustrative system comprising a pressure monitor.

A common problem encountered when using liquid (e.g., reaction fluids or components, such as a buffer) to propel a disposable container (DC) from the undeployed configuration (e.g., rolled) into the deployed configuration (e.g., unrolled) when filling the DC with liquid is ensuring uniform filling of DC such that it is maintained in a straight trajectory within its housing as it is being deployed. Depending on the type of material of which the DC is constructed (e.g., film stiffness and brittleness), it may bend or twist as it is being filled which causes significant delays and increases in costs. This disclosure provides DCs modified to maintain the DC in a straight (e.g., centered) orientation as it is being filled. In some embodiments, this disclosure provides DCs having at least two (i.e., at least a first and a second) internal chambers separated from one another, where at least one of said chambers is a reaction chamber (e.g., a first chamber or channel) and at least one second chamber (e.g., a second channel) can be inflated with a fluid (without inflating the other chamber) where the resulting pressure in the second chamber serves to deploy (e.g., unroll) the DC as the second chamber is filled to a suitable pressure (i.e., one that serves to deploy the DC). As the second channel is filled with a first fluid (e.g., air), the DC unrolls (e.g., is deployed), leaving the first chamber (i.e., reaction and/or buffer chamber) deployed (but unfilled; or potentially at least partially filled with reaction fluid(s)/component(s) and/or buffer or other fluid, such filling taking place either simultaneously with the filling of the second channel, or on a delayed schedule). For instance, in some embodiments, the DC comprises at least one welded channel (i.e., one or more welded channels, or second channel, or second chamber) along one or more of its perimeter(s). The weld serves to encapsulate the second chamber (e.g., providing a second channel) into which a non-reaction fluid (e.g., air) is introduced, and to separate this second channel from the first chamber (e.g., first channel, reaction chamber which is to receive reaction fluid(s)/component(s)) from one another. In such embodiments, the second channel can comprise a non-reaction fluid such as air, and the first channel (or reaction chamber) can comprise (or will comprise) reaction fluid(s)/component(s). In operation, the second channel can be filled (e.g., inflated) with a non-reaction fluid (e.g., air), and the pressure produced thereby in the first channel serves to deploy (e.g., unroll) the DC horizontally, e.g., along the bottom interior surface of the holder. In some embodiments, the inclusion of such a channel in the DC means that the DC material (e.g., the film) does not need to be folded and/or rolled in any particular way within the holder (or housing) in order to achieve a straight trajectory as it is deployed. Thus, in some embodiments, this disclosure provides DCs comprising one or more baffle(s) by allowing the perimeter channel along each seam to expand and remain expanded thus providing a baffle. In some embodiments, these arrangements also provide methods for testing the integrity of the seams of a DC (e.g., Single Use Container) from the outside (e.g., externally) without compromising the interior sterility or geometry of the DC. Such testing can be accomplished by, e.g., pressurizing the DC panels once deployed and challenging the internal/inboard weld of the DC. In some such embodiments, this disclosure provides a DC comprising at least a first chamber and at least one second chamber fluidly separated from one another, the first chamber being configured to contain a volume of fluid greater than that for which the second chamber is configured to contain, wherein at least partially filling the at least one second chamber with a fluid changes the configuration of the DC from an undeployed to a deployed configuration. In some embodiments, the at least one second chamber is at least partially filled with a non-reaction fluid (e.g., air) and the DC is an at least partially deployed configuration. In some embodiments, the DC comprises at least one perimeter area (e.g., edge(s)) wherein the at least one second chamber is positioned along, or at least partially along said perimeter(s). In some embodiments, the DC has an overall shape selected from the group consisting of circular, oval, square and rectangular. In some embodiments, the DC comprises a perimeter comprising at least two first edges and at least two second edges longer than said first edges, wherein at least one second chamber is at least partially positioned along at least one of said second edges. In some embodiments, the at least one second chamber is at least partially positioned along at least each of said second edges. In some embodiments, the at least one second chamber is at least partially filled with a non-reaction fluid (e.g., air and/or liquid, preferably air). In some embodiments, the first chamber is at least partially filled with a fluid (e.g., air and/or liquid, preferably liquid). This disclosure also provides systems comprising such DCs and further comprising a source of fluid with which the at least one second chamber can be at least partially filled; at least one fluidic pathway connecting said source of fluid and said at least one second chamber and, at least one valve for controlling the deposit and withdrawal of fluid (e.g., air and/or liquid, preferably air) from said at least one second chamber. In some embodiments, this disclosure also provides methods for deploying such DCs from an undeployed to a deployed configuration by providing (e.g., injecting or delivering) fluid (e.g., air and/or liquid, preferably air) to the at least one second chamber from a source of such fluid to at least partially fill said at least one second chamber such that the disposable container is deployed. In some embodiments, the disposable container comprises at least two second chambers that are each at least partially filled with said fluid (e.g., air and/or liquid, preferably air). An illustrative embodiment is shown in FIG. 4A. The illustrative system shown in FIG. 4A comprises a DC comprising a first chamber (4A-1) and two second chambers (4A-2; e.g., perimeter channels (partitions (4A-3)) fluidly separating the first and second chambers (meaning fluid is not exchanged between the first chamber and the second chambers thereby). An illustrative embodiment further comprising an air source from which air is injected into the second chambers through a series of fluidic connections (e.g., tubing) and controlled using valves and the like is shown in FIG. 4B. The DC in FIGS. 4A and 4B are illustrated in the deployed configuration. The DC may also comprise only a single second chamber, or more than two second chambers. For instance, in some embodiments, a single second chamber is positioned along one edge of the DC and as it is filled with a fluid (e.g., air), and that single second chamber can provide the force required to unroll the DC within a holder device (e.g., a vessel). In some embodiments, two, three, four, or more second chambers are variably positioned around the circumference and/or multiple edges of the DC. For instance, in some embodiments the DC is designed to deploy in a configuration comprising four corners (e.g., as a square or rectangle), and second chambers are positioned at at least two of such corners. In some embodiments, the second chambers can be positioned at each of the corners (e.g., four corners; see, e.g., FIG. 4C (as viewed from the front of the DC; 1: first chamber; 2: potential second chambers)). In some embodiments, the second chamber(s) may be a physically separate structure(s) that is inserted or otherwise affixed to the inner walls of the first chamber. Multiple second chambers that are fluidly separated from any one or more other second chamber (e.g., thus being non-contiguous with at least one other second chamber) can also be used (e.g., separately inserted or otherwise affixed to the inner walls of the first chamber). In some embodiments, the second chambers may be filled with fluid with or to the same or different amounts of fluid and/or pressures. As will be understood by those of ordinary skill in the art, the appropriate pressure to be maintained within the second chamber(s) depends in large part on the tension that pressure places upon the welds forming the second chamber and/or separating the first and second chamber(s). That tension is dependent on the radius of the chamber, the pressure within the chamber (i.e., placed upon the wall(s) thereof), the type of material of which the second chamber is formed, and the thickness of that material (e.g., of the walls of that chamber) which may be the same or different from that forming the main walls of the first chamber. For instance, in some embodiments, the pressure within the second chamber(s) may be, for example, any of 1, 2, 3, 4, 5, 6, 7, 8, 9, 10, or more pounds per square inch (psi). Once the DC is deployed (e.g. unrolled), the pressure in one (e.g., the one) or more of the second chamber(s) may be maintained or withdrawn, depending on the user's application. In addition, each second chamber may be connected to the same or different source(s) of fluid (e.g., air) and may be filled simultaneously and/or on an alternating schedule relative to one another. An exemplary method of operation is also described and illustrated in FIG. 4C as briefly summarized here: to deploy the DC, valve 2 (v2) can be opened while valve 1 (v1) is closed; air can then be pushed into the system using a blower ("Air in"); deployment can be stopped at PIT2 (0.2 PSIG), valve 3 (v3) closed and valve 4 (v4) opened to allow air to enter. Pressure tests may also be carried out as described therein and as illustrated in FIG. 5, and described in further detail below. Variations of these embodiments may also be suitable, as would be understood by those of ordinary skill in the art.

Another problem encountered by those of skill in the art relates to the limitation of the pressure within a DC to about 1 psi. When conducting leak tests, for example, one is limited by the sensitivity of the instruments on the tubing and/or pipework (e.g., to about 0.1 PSI or about 10%). In some embodiments, this disclosure provides for effectively measuring the pressure within the DC (1.0 PSIG) by transferring that pressure to a remote device via a fluidic connection (e.g., tubing) and measuring that pressure. For instance, in some embodiments, the remote device comprises a load cell captured using a bladder connected to the DC through a fluidic connection (e.g., tubing). In some embodiments, the pressure within the bladder is distributed across a load cell of greater surface area, thereby amplifying the signal, and essentially mirroring that within the DC. The systems described herein enable a greater sensitivity in pressure readings decoupled by, for instance, providing direct contact with the fluid (e.g., maintaining sterility as long as an appropriate sterile barrier (e.g., filter) is in place). In some embodiments, then, this disclosure provides such systems for measuring the pressure within a DC, where the system comprises at least one remote pressure monitor connected to the DC through a fluidic connection, the remote pressure monitor comprising at least one bladder for sampling fluid (preferably air) from the DC through the fluidic connection, a load cell, and at least one pressure indicating transmitter (PIT) that provides a representation of the pressure within the DC. In some embodiments, when the DC is maintained at atmospheric pressure, the PIT indicates a pressure of substantially zero. In some embodiments, when the DC is maintained at above atmospheric pressure, the PIT indicates a positive pressure. In some embodiments, the pressure within the DC is continuously monitored, and may be automatically continuously monitored. In some embodiments, this disclosure provides methods for monitoring and adjusting the pressure within a DC container by, for example: a) monitoring the pressure indicated by a pressure monitor connected to the DC through a fluidic connection, said pressure monitor comprising at least one bladder for sampling fluid from the DC through the fluidic connection, a load cell, and at least one pressure indicating transmitter (PIT) that provides a representation of the pressure within the DC; b) adjusting the pressure in the DC where the PIT indicates the pressure within the disposable container is too high; and, c) repeating steps a) and b) as required until an acceptable pressure within the DC is achieved. An illustrative embodiment is shown in FIG. 5. The embodiment shown therein provides a DC (maintained at either atmospheric pressure or 1 PSI), connected to both an air input and an exemplary remote pressure monitor comprising a bladder, a load cell, and a PIT, through a fluidic connection (tubing). As shown therein, the DC maintained at atmospheric pressure provides a load cell force of 0 kg. However, the DC maintained a pressure of 1 PSI provides a load cell force of 100 kg. The load cell force can be determined using, for example, the PIT. In some embodiments in which the DC comprises one or more second chambers with which the DC may be unrolled using (i.e., by filling the one or more second chambers with) a fluid such as air (e.g., by inflation), the second chambers may be deflated before beginning the leak test in order to, e.g., avoid placing too much tension on the welds of the one or more second chamber(s), or the first chamber. Variations of these embodiments may also be suitable, as would be understood by those of ordinary skill in the art.

Thus, in some embodiments, this disclosure provides a system(s) comprising: a DC comprising a first and second end, one or more attachment connectors at the first end, and one or more conveyance connectors at the second end; a holder comprising: upper and lower surfaces, and optionally side surfaces, each comprising an interior surface and an exterior surface; a front section and a rear section, each section comprising about one-half the length of the holder; one or more receiving connectors positioned near the front section for receiving the one or more attachment connectors of the disposable container; at least one mechanism for conveying the disposable container from the undeployed to the deployed configuration, optionally wherein the at least one mechanism is positioned closer to the rear section than the front section; and, at least one means of conveyance connected to the disposable container by the one or more conveyance connectors; wherein: the disposable container is positioned upon the inner surface of the holder, when the disposable container in the undeployed configuration, engagement of the means of conveyance changes the configuration of the disposable container to the deployed position wherein the disposable container is extended along at least part of the length of an inner surface of the holder; and, optionally, the means of conveyance is attached to the disposable container by the one or more conveyance connectors.

In some embodiments, this disclosure provides a reaction or container system(s) comprising: a disposable container comprising a first and second end, one or more attachment connectors at the first end, and one or more conveyance connectors at the second end; a holder comprising: an interior surface and an exterior surface; a front section and a rear section; optionally one or more side surfaces; one or more receiving connector(s) positioned near the front section for receiving the one or more attachment connectors, optionally upon the lower surface or sidewalls of the holder; wherein, optionally, the receiving connector is position on an inner surface and/or a sidewall; at least one orifice positioned near the rear section and connecting the inner surface and the outer surface; and, at least one means of conveyance traversing the orifice and being attached to the disposable container by the one or more conveyance connectors; wherein: the disposable container is positioned upon the inner surface of the holder, and attached thereto by the one or more attachment connectors; and, when the disposable container is positioned in the container in the undeployed configuration in the front section of the container and the means of conveyance is a cable: the one or more conveyance connectors are cable connectors positioned near the front section of the container; the cable extends through the orifice and along the inner surface of the holder to the front section and is attached to the disposable container by the one or more cable connectors; and, the application of a pulling force upon the cable from the rear section moves the cable connector and disposable container from the front section of the holder towards the rear section of the holder to position the disposable container in the deployed position.

In some embodiments, this disclosure provides such system(s), or reaction or container system(s), wherein: the disposable container and/or the holder are of an essentially square, rectangular, oval or circular shape; the one or more conveyance connectors are positioned closer to the front section of the holder than the back section; the disposable container is attached to the holder by the one or more attachment connectors; the means of conveyance is attached to the disposable container by the one or more conveyance connectors; the application of a pulling force upon the cable from the rear section moves the cable connector and disposable container from the front section of the holder towards the rear section of the holder to position the disposable container in the deployed position; when the disposable container is positioned in the container in the undeployed configuration within the front section of the container, the one or more conveyance connectors are positioned closer to the front section of the holder than the back section; the means of conveyance comprises one or more cables extending through an orifice positioned in the back section of the holder and along the inner surface thereof, the one or more cables being connected to the disposable container by the one or more conveyance connectors, one or more of the conveyance connectors optionally being a cable connector, and the application of a pulling force upon the cable from the rear section moves the cable connector and disposable container from the front section of the holder towards the rear section of the holder to position the disposable container in the deployed position; one or both of the one or more attachment connectors and/or the conveyance connector comprise a barb port; the mechanism for conveying the disposable container is one or more cables, one or more telescoping rods, and/or one or more screws; the mechanism for conveying the disposable container from the undeployed to the deployed configuration comprises an orifice in the holder and a cable connected to the disposable container and traversing said orifice; the mechanism for conveying the disposable container further comprises a manual or automatic cable roller; the cable extends through the orifice and is attached to the disposable container by the one or more conveyance connectors; the cable extends along the inner surface of the holder when the disposable container is in the undeployed position; the cable extends through the orifice and along the inner surface of the holder to the front section and is attached to the disposable container by the one or more cable connectors; the mechanism for conveying the disposable container comprises one or more pulleys; multiple units comprising at least one disposable container and at least one holder, optionally wherein the disposable container and/or holder of at least one unit is in contact with at least one disposable container and/or holder of at least one other unit; the disposable container is in fluid communication with at least one source of fluid that is deposited into the disposable container; the disposable container is in fluid communication with at least one reaction vessel; the disposable container is in fluid communication with at least one external source of fluid that is deposited into the disposable container, and is in further fluid communication with at least one reaction vessel; the disposable container comprises one or more fluids, optionally a buffer, within an interior chamber of the disposable container; the disposable container comprises at least one port, optionally multiple ports; the disposable container comprises multiple ports, at least one of said ports being in fluid communication with at least one source of fluid that is deposited into the disposable container and at least one of said ports is in fluid communication with at least one reaction vessel; and/or, at least one disposable container is in fluid communication with at least one other disposable container.

In some embodiments, this disclosure provides disposable container(s) (DC(s)) comprising one or more attachment connectors and one or more conveyance connectors; optionally wherein: the attachment connectors are suitable for attachment to a separate disposable container holder; the attachment connectors are suitable for attachment to a mechanism for conveying the disposable container from an undeployed to a deployed configuration within a disposable container holder; one or more of the connectors comprises a barbed port; the connectors are welded to the disposable container; the disposable container comprises an interior surface and an exterior surface, the interior surface surrounding at least one internal chamber, and said connectors are positioned on the exterior surface; the disposable container is comprised of two or more sheets of material adjoined to one another along at least one edge, and at least one or more of the connectors are positioned within at least one of said edges; the disposable container comprises a first end and a second end opposite the first end, the one or more attachment connectors are positioned at the first end, and the one or more conveyance connectors are positioned at the second end; the disposable container is attached to a disposable container holder by the one or more attachment connectors; the disposable container is attached to a mechanism for conveying the disposable container by the one or more conveyance connectors; the disposable container is attached to a mechanism for conveying the disposable container that is one or more cables, one or more telescoping rods, and/or one or more screws; the one or more attachment connectors and/or the one or more conveyance connectors comprise a barbed port; the disposable container has an essentially square, rectangular, oval or circular shape; the disposable container has a capacity of 10 to 10,000 liters, optionally 10 liters, 30 liters, 100 liters, 250 liters, 500 liters, 750 liters, 1,000 liters, 1,500 liters, 3,000 liters, 5,000 liters, or 10,000 liters; the disposable container is in fluid communication with at least one other disposable container; the disposable container is in fluid communication with at least one external source of fluid; the disposable container is in fluid communication with at least one reaction vessel; the disposable container is in fluid communication with at least one external source of fluid and at least one reaction vessel; the disposable container further comprises an interior chamber and comprising one or more fluids, optionally a buffer, within the interior chamber; the disposable container comprises at least one port, optionally multiple ports; the disposable container comprises multiple ports, at least one of said ports being in fluid communication with at least one external source of fluid and at least one of said ports is in fluid communication with at least one reaction vessel; and/or at least one of said ports is a barbed port.

In some embodiments, this disclosure provides a disposable container comprising at least a first chamber and at least one second chamber fluidly separated from one another, the first chamber configured to contain a volume of fluid greater than that for which the second chamber is configured to contain, wherein at least partially filling the at least one second chamber with a fluid changes the configuration of the disposable container from an undeployed to a deployed configuration; optionally wherein the at least one second chamber is at least partially filled with air and the disposable container in an at least partially deployed configuration; the disposable container comprising a perimeter wherein the at least one second chamber is positioned along at least partially along said perimeter; the disposable container has an overall shape selected from the group consisting of circular, oval, square and rectangular; the disposable container comprises a perimeter comprising at least two first edges and at least two second edges longer than said first edges, wherein at least one second chamber is at least partially positioned along at least one of said second edges; the disposable container comprises at least one second chamber at least partially positioned along at least each of said second edges; the disposable container comprises at least one second chamber is at least partially filled with a fluid; said fluid is a liquid such as air; and/or, said first chamber is at least partially filled with a fluid.

In some embodiments, this disclosure provides a system(s) comprising at least one disposable container, the system further comprising a source of fluid with which the at least one second chamber is at least partially filled, at least one fluidic pathway connecting said source of fluid and said at least one second chamber, and at least one valve for controlling the deposit and withdrawal of fluid from said at least one second chamber; optionally wherein said fluid is air.

In some embodiments, this disclosure provides method(s) for deploying a disposable container from an undeployed to a deployed configuration, the method comprising providing fluid to the at least one second chamber from a source of fluid to at least partially fill said at least one second chamber whereby the disposable container is deployed; optionally wherein the disposable container comprises at least two second chambers that are each at least partially filled with said fluid (e.g., air).

In some embodiments, this disclosure provides a system(s) and method(s) for measuring the pressure within a disposable container, the system comprising at least one remote pressure monitor connected to the disposable container through a fluidic connection, the remote pressure monitor comprising at least one bladder for sampling fluid from the disposable container through the fluidic connection, a load cell, and at least one pressure indicating transmitter (PIT) that provides a representation of the pressure within the disposable container; optionally wherein said fluid is air; when the disposable container is maintained at atmospheric pressure, the PIT indicates a pressure of substantially zero; the disposable container is maintained at above atmospheric pressure, the PIT indicates a positive pressure; and/or, the pressure within the disposable container is continuously monitored.

In some embodiments, this disclosure provides method(s) for monitoring and adjusting the pressure within a disposable reaction container, the method comprising: monitoring the pressure indicated by a pressure monitor connected to the disposable container through a fluidic connection, said pressure monitor comprising at least one bladder for sampling fluid from the disposable container through the fluidic connection, a load cell, and at least one pressure indicating transmitter (PIT) that provides a representation of the pressure within the disposable container; adjusting the pressure in the disposable container where the PIT indicates the pressure within the disposable container is too high; and, repeating these steps as required until an acceptable pressure within the disposable container is achieved.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

The term "combined" or "in combination" or "in conjunction" may refer to a physical combination of agents that are administered together or the use of two or more agents in a regimen (e.g., administered separately, physically and/or in time) for treating, preventing and/or ameliorating a particular disease.

All references cited within this disclosure are hereby incorporated by reference in their entirety. Certain embodiments are further described in the following examples. These embodiments are provided as examples only and are not intended to limit the scope of the claims in any way.

While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A disposable container horizontal deployment system comprising:
  a) a disposable container comprising a first and second end, one or more attachment connectors at the first end, and one or more conveyance connectors at the second end;
  b) a holder comprising:
    1. an upper surface, a lower surface, and side surfaces, each comprising an interior surface and an exterior surface thereof;
    2. a front section and a rear section;
    3. one or more receiving connectors, positioned in the front section, connected to the one or more attachment connectors of the disposable container; and,
    4. at least one mechanism for horizontally conveying the disposable container from an undeployed to a deployed configuration; and,
  c) at least one means of conveyance comprising one or more pulleys, cables, lines, strings, ropes, chains, treads, and/or telescoping rods connected to the disposable container by the one or more conveyance connectors;

wherein:
  i) the disposable container is positioned upon an inner surface of the holder, and,
  ii) when the disposable container is in the undeployed configuration, engagement of the at least one means of conveyance changes the undeployed configuration to the deployed configuration wherein the disposable container is extended horizontally along the interior surface of the upper surface, and/or side surfaces of the holder.

2. The disposable container horizontal deployment system of claim 1 wherein:
  the disposable container and/or the holder are of an essentially square, rectangular, oval or circular shape;
  the one or more conveyance connectors are positioned closer to the front section of the holder than the rear section;
  the disposable container is attached to the holder by the one or more attachment connectors;
  when the disposable container is positioned in the container in the undeployed configuration within the front section of the container, the one or more conveyance connectors are positioned closer to the front section of the holder than the rear section, the one or more cables of the at least one means of conveyance extend through an orifice
  positioned in the rear section of the holder and along the inner surface thereof, the one or more cables being connected to the disposable container by the one or more conveyance connectors, one or more of the conveyance connectors optionally being a cable connector, and, the application of a pulling force upon the cable connector from the rear section moves the cable connector and disposable container from the front section of the holder towards the rear section of the holder to position the disposable container in the deployed configuration.

3. The disposable container horizontal deployment system of claim 1 wherein:
  one or both of the one or more attachment connectors and/or the conveyance connector comprise a barb port; and/or,
  the disposable container:
    is in fluid communication with at least one reaction vessel; and/or
    is in fluid communication with at least one external source of fluid that is deposited into the disposable container, and is in further fluid communication with at least one reaction vessel; and/or
    comprises one or more fluids, optionally a buffer, within an interior chamber of the disposable container; and/or
    comprises at least one port, optionally multiple ports;
    comprises multiple ports, at least one of said ports being in fluid communication with at least one source of fluid that is deposited into the disposable container and at least one of said ports is in fluid communication with at least one reaction vessel.

4. The disposable container horizontal deployment system of claim 1 wherein the at least one mechanism is positioned closer to the rear section than the front section.

* * * * *